Figure 1:
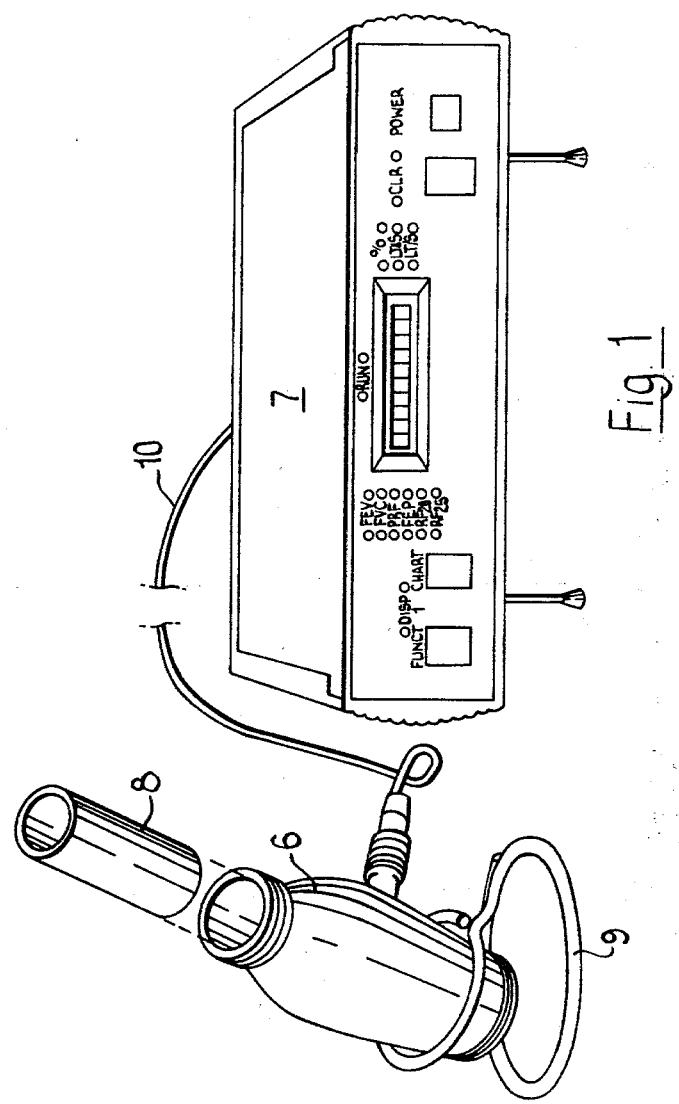

United States Patent [19]

Yerushalmy

[11] 4,282,883

[45] Aug. 11, 1981

[54] SPIROMETERS

[75] Inventor: Moshe Yerushalmy, Turramurra, Australia

[73] Assignee: Scitec Corporation Ltd., Sydney, Australia

[21] Appl. No.: 51,897

[22] Filed: Jun. 25, 1979

[30] Foreign Application Priority Data

Jul. 3, 1978 [AU] Australia ............................. PD4924

[51] Int. Cl.³ .............................................. A61B 5/08
[52] U.S. Cl. ................................ 128/726; 73/861.77; 73/861.92
[58] Field of Search ....................... 128/726, 725, 716; 73/229–231, 861.77, 861.79, 861.85, 861.91, 861.92, 861.94

[56] References Cited

U.S. PATENT DOCUMENTS

| | | | |
|---|---|---|---|
| 3,217,539 | 11/1965 | Owen et al. | 73/231 R |
| 3,636,767 | 1/1972 | Duffy | 73/229 |
| 3,680,378 | 8/1972 | Aurilio | 128/726 X |
| 3,709,037 | 1/1973 | Abbotts | 73/231 |
| 3,811,323 | 5/1974 | Swenson | 73/231 R |
| 3,922,525 | 11/1975 | Kozak et al. | 128/725 X |
| 4,034,743 | 7/1977 | Greenwood et al. | 128/725 |
| 4,122,842 | 10/1978 | Pikol | 128/725 |
| 4,132,453 | 1/1979 | Bumis et al. | 73/231 R X |
| 4,158,360 | 6/1979 | Adams | 128/725 |

FOREIGN PATENT DOCUMENTS 898147 6/1962 United Kingdom ................. 73/231 R

OTHER PUBLICATIONS

Schneiderreit, "The Turbulence Respirometer . . . ", Biomed. Technik, vol. 21, No. 8, pp. 228–230, Oct. 1976.

Primary Examiner—Lee S. Cohen
Attorney, Agent, or Firm—Irvin A. Lavine

[57] ABSTRACT

A spirometer having a turbine transducer which includes a plurality of blades past which exhaled or inhaled air can be blown on sucked to cause a degree of rotation of the blades in proportion to the volume of air passing at a speed proportional to the rate of flow of the air. The turbine transducer produces a series of electrical pulses preferably by an electro-optical sensor at a rate proportional to the rate of rotation of the blade and these are fed to a microprocessor which stores and processes pulses and displays information relating to pulmonary functions calculated in the microprocessor. It is preferred that the turbine transducer is housed in a body that can be held in the hand of and raised to the mouth of a patient and is constructed in such a manner and of such materials as to make it readily dismountable for cleaning while responding quickly and accurately to changes in the rate of flow of exhaled or inhaled air.

5 Claims, 7 Drawing Figures

SPIROMETERS

The present invention relates to a spirometer and more particularly to a spirometer incorporating a turbine transducer coupled with a micro processor system.

An object of the invention is to provide a small light weight, portable spirometer utilizing a turbine flow measurement technique, the turbine being a direct displacement system responding quickly and accurately to changes in rate of flow of air exhaled or inhaled and which provides through a sensor an input to a micro processor system by means of which a very wide variety of functions such as peak rate of flow (PRF), forced expiratory volume in 1 second (FEV1) and forced vital capacity (FVC), may be stored and presented upon command in a variety of different ways.

Figure 3:
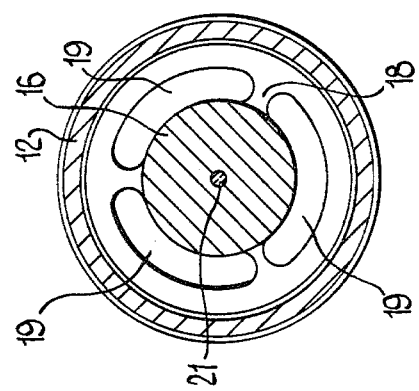
Figure 2:
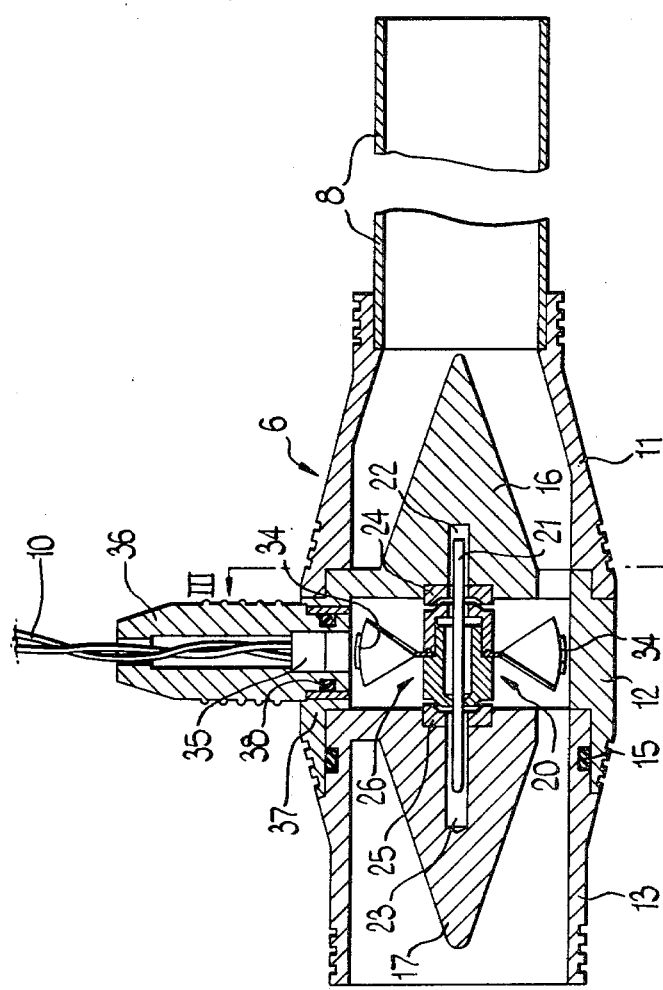
Figure 4:
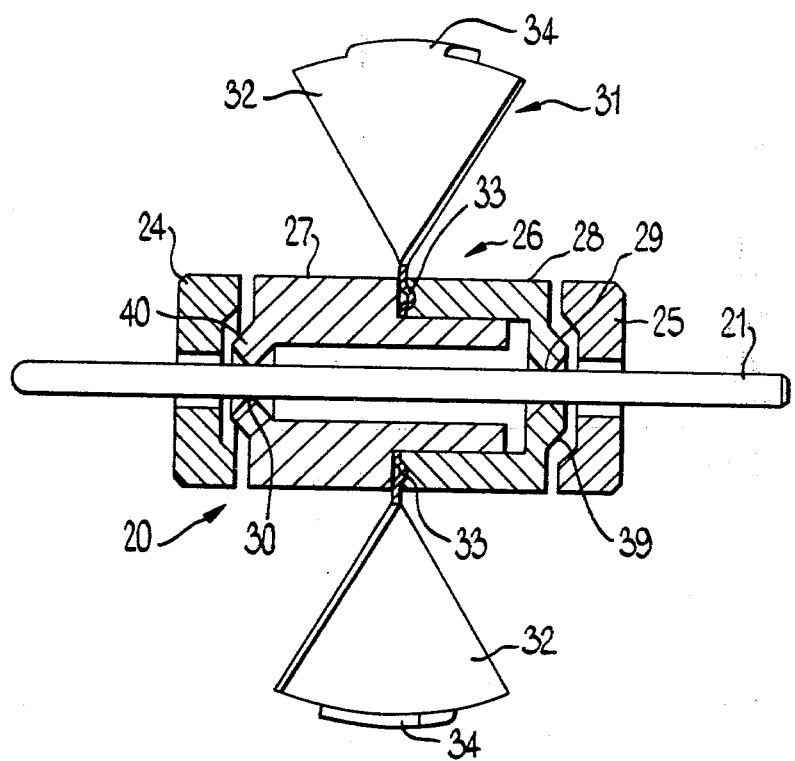
Figure 6:
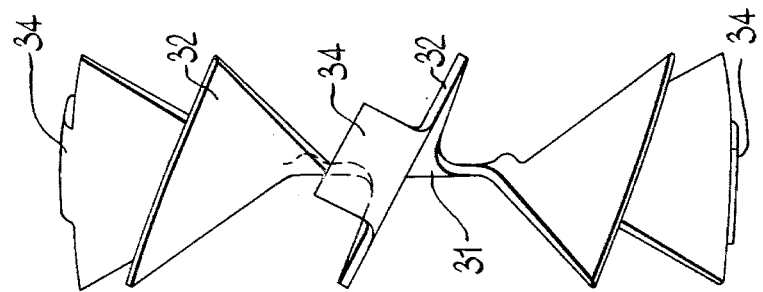
Figure 5:
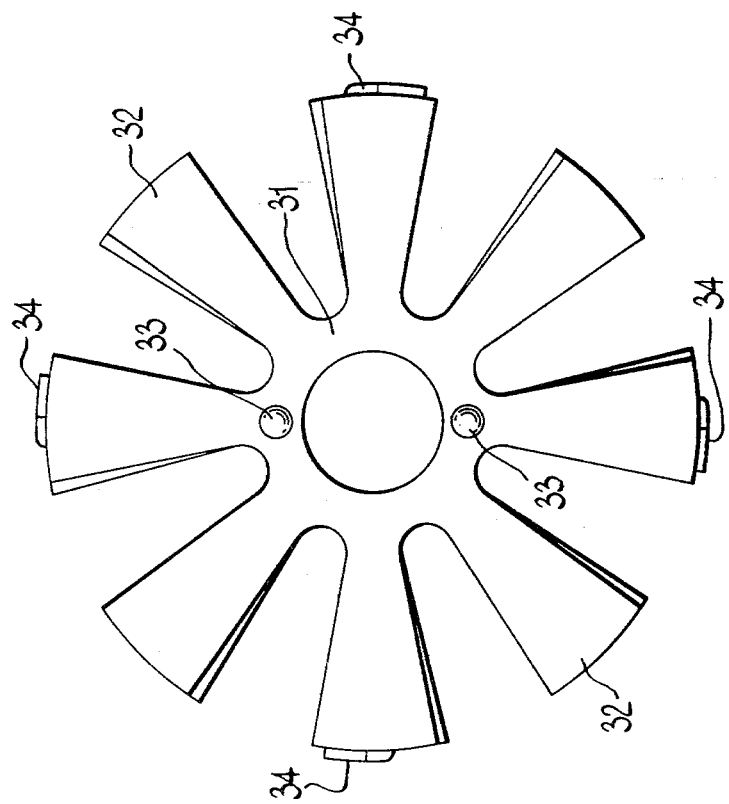
Figure 7:
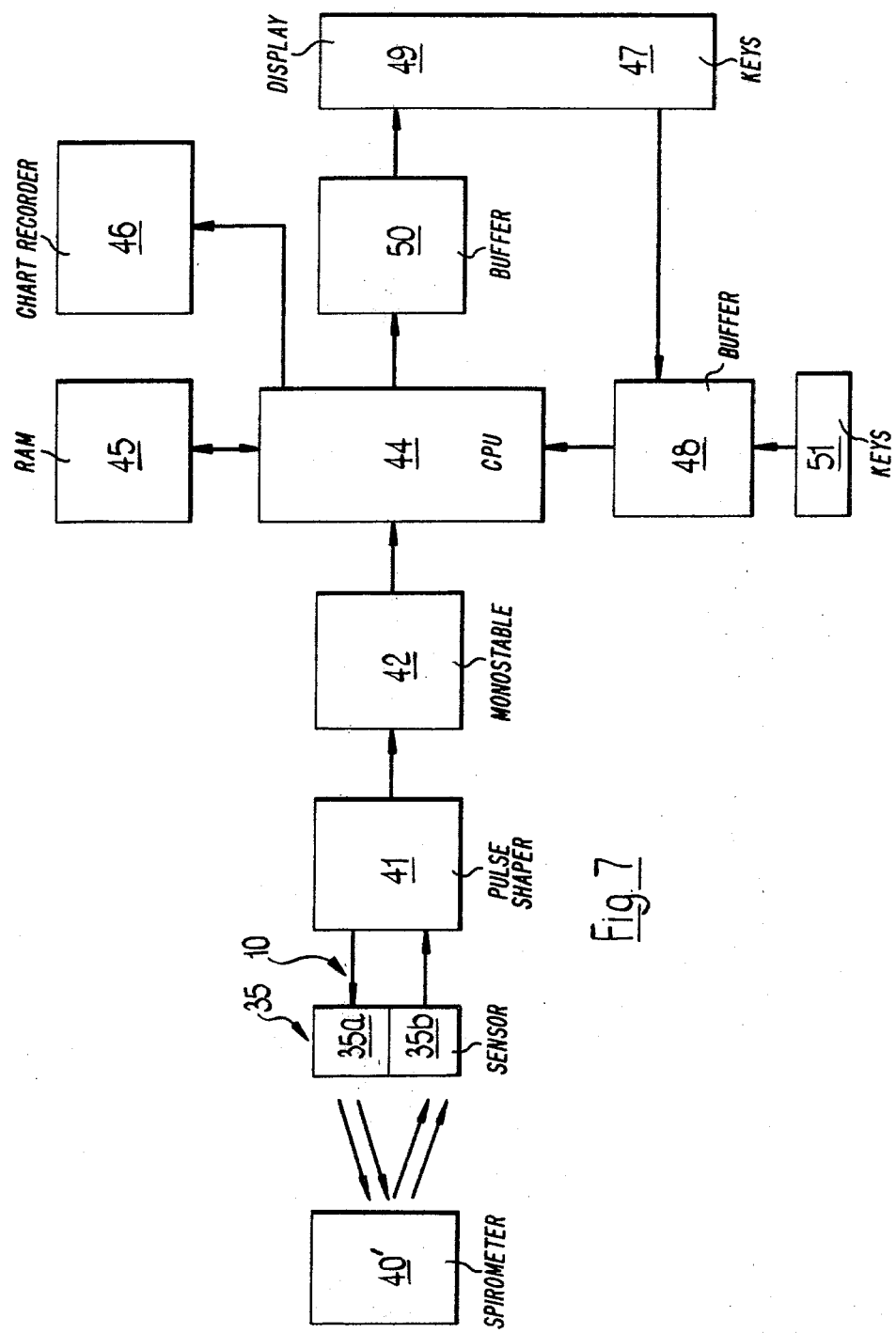

In order that the invention may be better understood and put into practice a preferred form thereof is hereinafter described by way of example with reference to the accompanying drawings in which:

FIG. 1 illustrates the essential components of a spirometer according to the present invention, FIG. 2 is a longitudinal cross-sectional view of the turbine transducer of the spirometer, FIG. 3 is a sectional view of the turbine transducer on line III—III of FIG. 1, FIG. 4 is a sectional view of the turbine transducer rotor assembly to an enlarged scale, FIG. 5 is a view in elevation of the turbine blades, FIG. 6 is a side view of the turbine blades, and FIG. 7 is a block diagram of the circuitry of the micro processor unit.

FIG. 1 shows the essential parts of a spirometer according to the invention these being a turbine transducer 6 and a micro processor and digital display unit 7. The turbine transducer 6 is designed to be held in the hand of a patient while air is exhaled from the lungs or inhaled into the lungs through the replaceable cardboard tube 8 of the kind conventionally used with spirometers. The body of the turbine transducer is made of light-weight material such as aluminium alloy or plastic and, as will be explained in more detail below, can be readily dismantled for cleaning and equally readily reassembled. When not in use the turbine transducer is supported on the small wire stand 9. The turbine transducer 9 and the micro processor unit 7 are connected by a flexible lead 10 of suitable length so that the turbine transducer can be lifted in the hand and held by a patient against his mouth.

FIG. 2 shows in detail the general constructional features of the turbine transducer 10. This consists of a body made in three parts 11, 12 and 13 defining between them an axially extending passage. In a preferred form of the invention these are made in aluminium alloy which is externally anodized against corrosion. The parts 11 and 12, while being manufactured separately, are joined in manufacture so as to constitute a single unit. The part 13 may however be readily separated from the part 12, the joint between them being sealed by the O-ring 15. Ease of dismantling and reassembly is particularly important, as the internal parts of the turbine transducer must be cleaned regularly owing to the contamination that occurs during expiration of air through the transducer. The part 11 receives one end of the cardboard tube 8 which is replaced each time the apparatus is used. The part 12 supports a conical diffuser 16 which is formed integrally with it. The part 13 supports a similar conical diffuser 17 formed integrally with it, the conical diffuser 16 and 17 being arranged co-axially base to base with a space between them.

As will be seen from FIG. 3 the diffuser 16 is supported from the part 12 by three radially extending portions 18 leaving between them apertures 19 through which air can pass. The diffuser 17 is supported in a similar manner from the part 13, to provide similar aperture for the flow of air.

The diffusers 16 and 17 support between them a turbine rotor assembly indicated generally at 20 and shown to a larger scale in FIG. 4. The assembly consists of a stainless steel axle 21 which is held non-rotatably but removably in axial passages 22 and 23 in the diffusers 16 and 17 respectively. These diffusers also carry cheek pieces 24 and 25 on their bases. As will be seen from FIG. 4 these do not make contact with the axle 21 and, as will be described below, constitute thrust bearings for the assembly. Supported on the axle 21 is the turbine assembly 26 made up of two co-axial interengaging parts 27 and 28 which are interconnected in the manner shown in FIG. 4, the part 27 being a press fit inside the part 28. These are supported on the axle 21 so as to rotate thereon by the narrow annular bearing surfaces 29 and 30 which, in the preferred form of the invention have a width of ½ mm. The parts 27 and 28 support between them a blade carrying member 31 having on it a plurality of radially extending blades 32 made preferably from a light material such as aluminium alloy or plastic. This member is best seen in FIG. 5. Relative rotation between the blade carrying member 31 and the part 28 is prevented by the dimples 33 formed on the member 31 which engage in corresponding part-spherical cavities in the part 28. Alternate turbine blades 32 carry small plates 34 at their tips; these extend from the blades so as to lie substantially parallel with the axis of the axle 21. The plates 34 act in conjunction with an electro-optical sensor 35. This consists basically of an infra red source and a photo diode, the infra red source producing rays which are directed in such a manner that, if a reflecting surface is presented at an appropriate distance, the rays are reflected back to the diode but not otherwise. This sensor operates in connection with the plates 34 in such a manner that as the turbine blades rotate, each time one of the plates 34 passes across the field of the sensor 35, a pulse is transmitted down the lead 10 to the micro processor unit 7.

The sensor 35 is mounted in the optics plug 36 which plugs into the aperture 37 in the part 12 the joint being sealed by the O-ring 38. This arrangement enables the optics plug to be readily removed when the apparatus is dismantled for cleaning. It is to be noted that the sensor 35 is set some way into the optics plug 36. The purpose of this is to make it unaffected so far as possible by ambient light entering the interior of the turbine transducer.

The method of construction of the turbine bearing assembly forms an important part of the apparatus in that an essential feature for the proper functioning of a low rate of flow turbine is for the friction in the moving parts to be very small, a result that is achieved by the bearing assembly described. The parts of it are made preferably of the plastic material known as PTFE, which has very low friction characteristics. To reduce wear the PTFE is preferably mixed with 25% of electrographitised carbon. The resulting material has all the desirable characteristics for its intended purpose providing low friction, resistance to wear and resistance to fluids necessary for cleaning the interior of the turbine transducer. An alternative material is that sold under the trade mark 'DELRIN'.

An alternative approach is to make the parts of the turbine bearing assembly, notably 24, 25, 27 and 28, of stainless steel. By proper machining techniques this can be provided with the proper friction characteristics in relation to the stainless steel axle 21 and is likely to reduce manufacturing costs.

Whereas conventional practice is to construct turbines for such purposes with a rotating shaft supported by diamond or other watch type bearing materials, it is found that such bearings are hard to adjust and keep clean and that moisture and water vapour necessarily present in a spirometer affect their performance. The use of a fixed axle made preferably of stainless steel carrying a rotatable bearing assembly as described has been found most satisfactory. In order to deal with the axial forces acting on the bearing assembly during exhalation or inhalation the parts 27 and 28 are provided with narrow annular bearing surfaces 39 and 40 which bear on the cheek pieces 25 and 24 respectively depending on the direction of thrust.

It has been found that with the bearing assembly described above a very low initial frictional resistance to the turning of the turbine is provided and it is thus possible to read very low rates of flow. In a practical example it was found possible to read a rate of flow as low as 0.04 liters per second of air.

For optimum results it is necessary not only to have very low friction in the bearing assembly but for the blades to be set at an angle such that rotation will commence at the lowest possible air speed and it has been found that the angle made by that portion of the blades of the turbine lying between the two sets of apertures 19 that come under the influence of the air flow, with the axis of the axle 21 (see FIG. 6), should be about 28°. It was found that if the angle is increased to 35° or 40° the turbine is insufficiently sensitive to low flow rates and if the angle is decreased below 20° turbulence occurs and the turbine tends to flutter. In the design of the turbine blades it is desirable that the part of the blade under the aerodynamic force is set at a large radius from the axis. This radius is however limited by considerations of lightness, in that the greater the inertia of the moving parts the less the ability of the instrument to follow rapid fluctuations in the rate of flow of the air. Moreover, the resisting frictional torque is comprised partly of a torque due to the weight of the moving parts, partly of a torque due to end thrust. The first of these factors will increase with the weight of the blades and the second with their size and it is necessary to reach a compromise in a practical design. The second factor is dealt with by the design of the bearing in the manner described above.

Optimisation of the air flow through the turbine transducer is necessary in view of the low rate of flow normally involved and with this in view it is necessary firstly that the apex angle of the conical diffusers 16 and 17 shall be between 35° and 40°, optimum results being obtained at 38°. This angle has been obtained empirically. The air passage defined between the conical diffusers and the body of the turbine transducer must be such as to avoid turbulence in the flow and the area of the apertures 19 through which the air flows to the turbine blades is desirably equal to the internal cross-sectional area of the inlet tube 12 so that the rotation of the turbine blades is directly related to the volume of air passing through the apparatus. It is to be noted that the turbine transducer is approximately symmetrical in configuration so that it will serve equally well in respect of exhaled and inhaled air. A slight assymetry will be noted in the shape of the conical diffusers 16 and 17 in that the diffuser 17 is given a slightly greater tip radius. This is not a feature of any significance and is done to reduce the possibility of damage to the tip of the diffuser 17. The annular space around the diffuser 16 is shaped slightly differently from that around the diffuser 17 the outer wall initially being substantially parallel with the surface of the conical diffuser 16 and thereafter proceeding axially to direct the flow in an axial direction.

FIG. 7 shows by means of a block diagram the general arrangement of the micro processor. In this diagram the mechanical parts of the spirometer described above are indicated at 40'. Adjacent to this is the sensor 35 consisting of an infra red source 35a and a photo diode 35b. These are available as a standard item of equipment constructed as a single assembly. A preferred example of such an assembly is that manufactured by the Fairchild Corporation under reference FPA103. This is connected by the flexible lead 10 to the first element of the micro processor which is a pulse shaper 41. As the turbine rotates a pulse is produced as each alternate blade passes the sensor 35 and these pulses pass to the pulse shaper 41 and are then standardised in amplitude by a monostable device 42. Each standardised pulse is then used as an indicator to activate the pre-programmed micro processor's central processing unit 44 which times out the interval between each pulse received, stores each time interval in a random access memory 45, accumulates the total number of impulses received periodically over a complete patient test and stores these accumulations and continually updates the position of a chart recording pen on a chart recording means 46 throughout the test, to display a chart recording of volume of air flow against time. The central processing unit 44 is programmed to determine the start and finish of the test by comparative measurement of time duration of consecutive pulses. On completion of a test, the central processing unit 44 enters a "calculation" phase in its programme and automatically calculates all required pulmonary functions for the completed test and stores these values in a memory resident within the central processing unit 44. On completion of the "calculation" phase, the central processing unit 44 is programmed to enter a "display" phase in which, on command from a front panel key means 47, via an input buffer 48, all stored pulmonary functions may be displayed in sequence on a numerical indicator display 49, via an output buffer 50. Further to these functions a second key means 51 is provided to command the central processing unit 44 via the input buffer 48 to display a chart recording on the chart recorder 46 of rate of air flow against time. A key incorporated in 47 is used to "reset" all memory and display, ready for a new test. The "reset" condition is the default condition on "power-up".

It is not proposed to describe the electronic circuitry illustrated diagrammatically in FIG. 2 in more detail as this follows conventional digital processing procedures well known to those skilled in the art. The programming of the central processing unit 44 will depend on the pulmonary functions that it is desired to display. A reference was made at the beginning of this specification to two of these, namely FEV1 and FVC. However, the input to the micro processor system enables a whole range of pulmonary functions to be displayed and it is considered unnecessary to recite these as they are all derivatives of the basic calculations made by the micro processor system. During a given test the number of revolutions the turbine produces during that test is noted by the photo optic sensor which produces a number of pulses proportional to the number of blades displaced during the test. The central processing unit 44 receives this data, counts the number of pulses in the first second and multiplies both this number and the total number of pulses by a constant number programmed into the unit. (This number represents volume in fractions of liters arrived at by measuring displacement of a known volume.) At the same time the processor is looking for the shortest time interval between each pulse, this interval represents the peak rate of flow since it means that a known given volume has passed the fastest through a constant section of the tube. From these basic facts a very wide variety of pulmonary functions may be computed.

Reference is made above to a chart recorder. It is, however, not essential that a chart recorder be provided as in some cases it will be sufficient for the various functions to be given on a digital display incorporated in the micro processor system.

In addition to a chart recorder a visual display unit may be provided for use at hospital, clinic and specialist levels. In such a case the system may comprise a visual display unit and a front key board for entering information and commanding various displays. The volume/time, flow/time and flow/volume (loop) functions will be displayed on a television screen and all test functions will be displayed similarly. It is contemplated that such a unit will have an inbuilt chart recorder so that the various graphs can be kept as hard copies and a printer will be provided for hard copy test results. An analogue output will be provided for an X-Y recorder as well as a computer serialised data so that hospitals and clinics can store information in major computers, if so desired. Accessories such as a cassette recorder or a floppy disk system may be provided so that records of information may be stored in-house and redisplayed for test comparison. The construction of such a unit follows conventional lines and will therefore not be described in detail.

I claim:

1. A turbine transducer for a spirometer comprising a hollow body adapted to be held in the hand of and raised to the mouth of a patient, said body having an axially extending passage throughout its length,
   means on the body at one end of said passage to receive a removable tube through which the patient can exhale air into said passage,
   a pair of conical diffuser members each having a cone angle of between 35° and 40°,
   means supporting said diffuser members in said passage coaxially, base to base, and spaced apart,
   a turbine rotor assembly,
   means mounting said turbine rotor assembly in the space between said conical diffuser members for rotation about the axis of said passage,
   said turbine rotor assembly including a plurality of radially extending blades, said blades having portions exposed to the movement of air through the said passage extending at an angle of between 20° and 40° to the axis of rotation of the turbine assembly, selected ones of said blades having a portion directed toward the wall of said passage and lying adjacent thereto,
   means defining apertures in said diffuser members supporting means permitting passage of air past said conical diffuser members to said blades to cause rotation of the turbine rotor assembly at a rate directly related to the rate of flow of air in said passage,
   photo-optical sensor means,
   an aperture in the side of said body opposite said blades,
   means supporting said photo-optical sensor means in said aperture in said body allowing the photo-optical sensor means to direct radition onto each said blade portion directed towards the wall of said passage and to receive radiation reflected from each said blade portion during its passage past said photo-optical sensor means and thereby produce an electrical pulse,
   said body being made in at least two separate parts, each part including one of said conical diffuser members and a part of said means for mounting said turbine rotor assembly,
   whereby the transducer may be dismantled and the turbine assembly removed for cleaning.

2. A turbine transducer for a spirometer as claimed in claim 1, wherein the said cone angle is 38°.

3. A turbine transducer for a spirometer as claimed in claim 1, said turbine rotor assembly comprising two co-axial interengaging members, a blade carrying member mounted between said interengaging members, said mounting means for said turbine rotor assembly comprising spaced-apart narrow annular bearing surfaces on said interengaging members, a shaft extending through said annular bearing surfaces and rotatably supporting said turbine rotor assembly, and said diffuser members comprising means for non-rotatably supporting said shaft.

4. A turbine transducer as in claim 3, each said conical diffuser member having at the base thereof an annular cheek member of low friction plastic, each said interengaging member having at an end thereof a narrow annular bearing surface positioned for engaging a said cheek member under axial thrust.

5. A turbine transducer as in claim 1, wherein said portions of said blades extend substantially parallel to the axis of said turbine rotor assembly.

* * * * *